(12) United States Patent
Wiener et al.

(10) Patent No.: US 8,395,129 B2
(45) Date of Patent: Mar. 12, 2013

(54) CHAMFERED PALLET FOR NUCLEAR MEDICINE

(75) Inventors: Jason S. Wiener, Fremont, CA (US); Merlene Robergeau, San Jose, CA (US); Jody L. Garrard, Elk Grove, CA (US); Raymond C. D'Ambrosio, Fremont, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 524 days.

(21) Appl. No.: 12/599,101

(22) PCT Filed: Apr. 17, 2008

(86) PCT No.: PCT/IB2008/051484
§ 371 (c)(1),
(2), (4) Date: Jul. 19, 2010

(87) PCT Pub. No.: WO2008/139345
PCT Pub. Date: Nov. 20, 2008

(65) Prior Publication Data
US 2012/0267542 A1  Oct. 25, 2012

Related U.S. Application Data

(60) Provisional application No. 60/917,184, filed on May 10, 2007.

(51) Int. Cl.
*G01J 1/42* (2006.01)

(52) U.S. Cl. .............. 250/395; 250/393; 250/363.01; 250/362

(58) Field of Classification Search ............ 250/395, 250/358.1, 393, 363.04, 366, 363.01
See application file for complete search history.

(56) References Cited

U.S. PATENT DOCUMENTS

| 5,097,132 | A | 3/1992 | Plummer |
| 7,159,832 | B2 | 1/2007 | Easterling |
| 2004/0133980 | A1 | 7/2004 | Coppens et al. |
| 2006/0016006 | A1 | 1/2006 | Whitmore, III et al. |

FOREIGN PATENT DOCUMENTS

| WO | 2004064700 A1 | 8/2004 |
| WO | 2006026646 A1 | 11/2009 |

*Primary Examiner* — Edwyn Labaze

(57) ABSTRACT

A pallet (10) for use with a gamma camera includes a rigid sheet (30) having a thickness (d) of less than six millimeters and a strength-enhancing curvature transverse to an axial direction (DA). At least a portion of an edge (32) of the rigid sheet has a bevel (B) with a length (x) along the sheet of at least about ten millimeters and a height (y) of at least about four-fifths of the sheet thickness. A protective covering (34) is disposed over the beveled edge. In a nuclear imaging method, a subject is disposed on the rigid sheet and a radiological image is acquired of at least a portion of the subject disposed on the sheet with at least one radiation detector head (8) positioned underneath or at an oblique angle below the subject. The bevel is effective to reduce or blur an edge artifact in the acquired image.

23 Claims, 6 Drawing Sheets

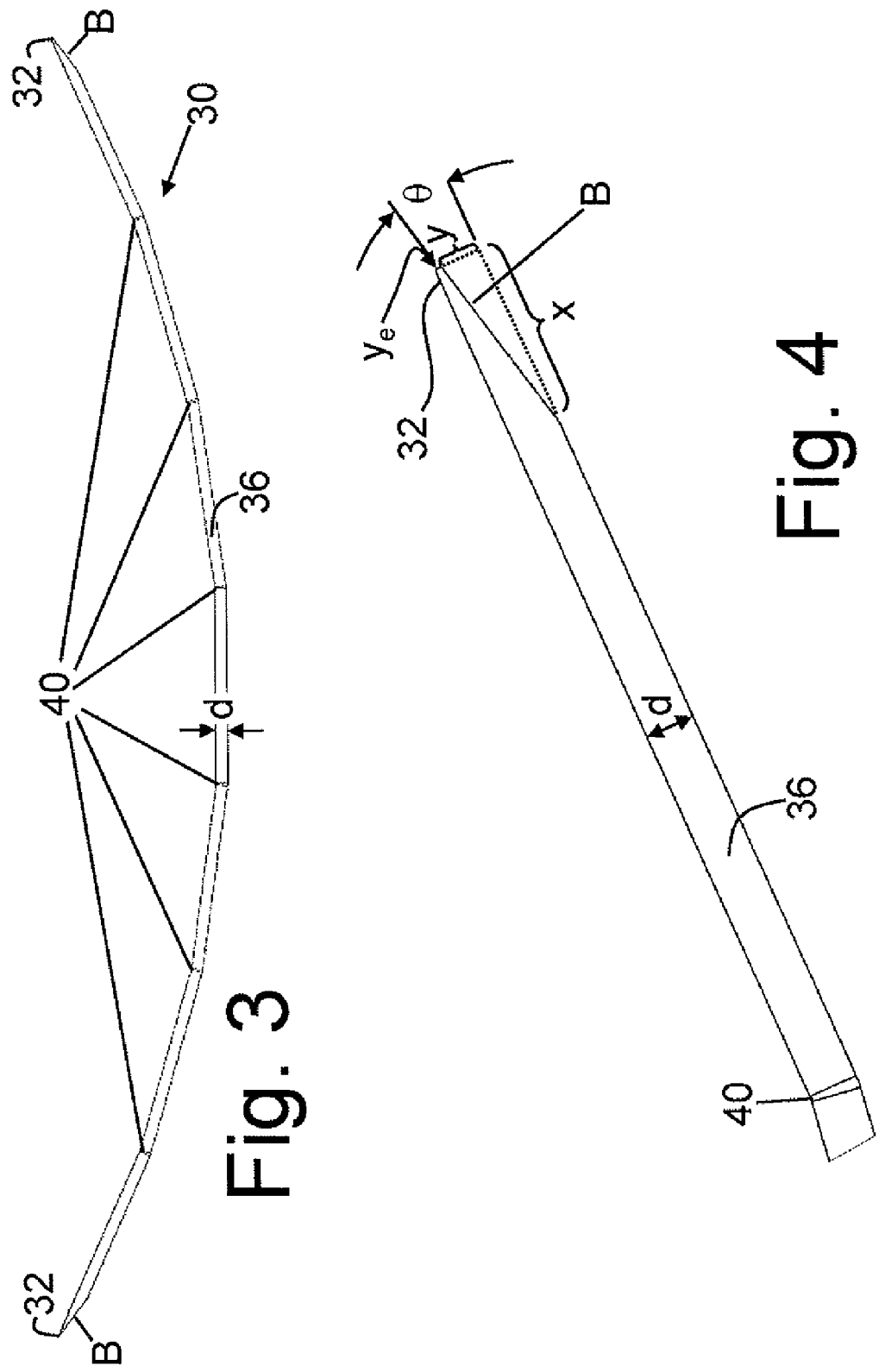

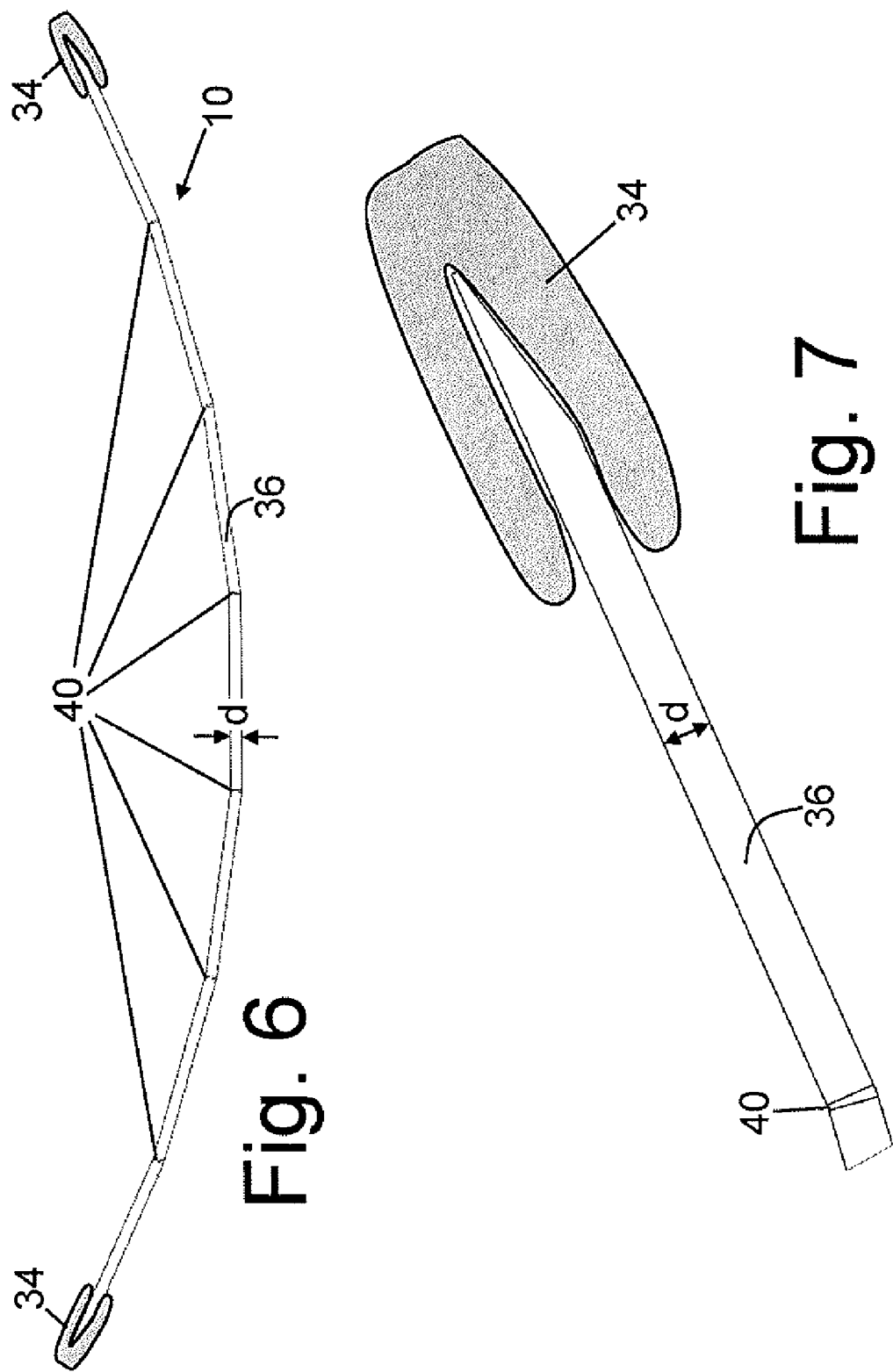

CHAMFERED PALLET FOR NUCLEAR MEDICINE

CROSS REFERENCE TO RELATED APPLICATIONS

This application claims the benefit of U.S. provisional application Ser. No. 60/917,184 filed May 10, 2007, which is incorporated herein by reference.

The following relates to the nuclear medicine arts. It particularly relates to planar imaging of the spine, torso, or other regions. However, the following will find more general application in nuclear medicine generally, including planar scans of various types, single photon emission computed tomography (SPECT) imaging, and so forth.

In nuclear medicine, a radiopharmaceutical is administered to a subject. The radiopharmaceutical is typically configured to preferentially aggregate in a tissue or organ of interest, such as the bones, blood, lungs, or so forth. Radiation emitted by the radiopharmaceutical is detected by radiation detector heads of a gamma camera to generate an image. Because the radiopharmaceutical is a radioactive substance, the dosage of administered radiopharmaceutical must be carefully controlled and relatively low. As a consequence, the detectable signal from the administered radiopharmaceutical is weak.

To enable high resolution imaging using a weak signal, the detector heads should be highly sensitive, and should be placed as close as feasible to the subject during imaging data acquisition. In scans in which one or more detector heads are positioned underneath or at an oblique angle below the patient, or during tomographic scans in which the detector heads move generally conformally around the subject, the thickness of the pallet supporting the subject is a concern.

The pallet is advantageously made thin to enable the detector heads to be positioned close to the patient; yet, the pallet should be strong enough to rigidly support the subject in a cantilevered or double-end supported configuration. Existing pallets made of planar aluminum or carbon fiber sheets have a thickness of about 2-4 millimeters, and are bent or curved transverse to the axial direction to enhance structural strength and better support the subject. In some existing pallets, the edges of the pallet are thicker than the center—the thin central region of the pallet is advantageous for spine imaging, while the thicker edges provide enhanced structural strength to compensate for the thinness of the central region of the pallet.

Safety is a concern with such thin pallets, because the 2-4 millimeter thick squared edges have sharp corners, and can cut the subject or attending medical personnel. In some pallets, the pallet edges are formed by the sheet cutting, and have sharp right angles that can produce cuts. Some pallets use buffing or other mechanical smoothing to smooth or round the corners enough so as to reduce this risk of injury. Even with such smoothing, the thinness of the pallet edges presents some safety risk.

The edges of the pallet are also known to generate abrupt linear artifacts in planar images acquired using detector heads located underneath or obliquely below the subject. These linear artifacts are caused by the abrupt change in attenuation of the radioactive emissions at the pallet edge. Rounded pallet edges have not been found to reduce such artifacts, because the rounded edge of a 3-4 millimeter pallet still presents an abrupt attenuation transition on the order of about one-half to two millimeters or less. Such an abrupt attenuation transition is comparable with the image resolution. The presence of an abrupt linear artifact from the edge of the pallet can be problematic for diagnostic applications. A physician or other diagnostician may mistake the edge artifact for anatomical structure, or the edge artifact may obscure underlying anatomical structure.

The following discloses improvements which overcome the above-referenced problems and others.

In accordance with certain illustrative embodiments disclosed herein as examples, a pallet is disclosed for use in conjunction with a gamma camera with a finest resolution $R_F$. The pallet includes a rigid sheet with a bevel defined along at least a portion of a longitudinal edge of the rigid sheet. The bevel has a length transverse to the longitudinal edge which is at least about ten times larger than the finest resolution $R_F$ of the gamma camera.

In accordance with certain illustrative embodiments disclosed herein as examples, a pallet is disclosed for use in conjunction with a gamma camera. A rigid sheet has a thickness of less than six millimeters and a strength-enhancing curvature transverse to an axial direction. At least a portion of an edge of the rigid sheet has a bevel with a length along the sheet of at least about ten millimeters and a height of at least about four-fifths of the sheet thickness.

In accordance with certain illustrative embodiments disclosed herein as examples, a nuclear imaging method is disclosed. A subject is disposed on a rigid sheet having strength-enhancing curvature transverse to an axial direction, a thickness of less than six millimeters, and a high aspect ratio bevel in at least one edge of the rigid sheet. A radiological image is acquired of at least a portion of the subject disposed on the rigid sheet. The high aspect ratio bevel is effective to reduce or blur an edge artifact in the image when the image is acquired at least partly from underneath or at an oblique angle below the subject.

In accordance with certain illustrative embodiments disclosed herein as examples, an imaging system is disclosed. A subject support pallet includes a rigid sheet having strength-enhancing curvature transverse to an axial direction. An edge of the rigid sheet has a bevel with an aspect ratio x:y where dimension "x" is along the rigid sheet and is at least ten millimeters and "y" is transverse to the sheet and is at least about four-fifths of a thickness of the rigid sheet. A pallet support is configured to support the subject support pallet generally horizontally in an elevated position respective to a floor. At least one radiation detector head is selectably locatable at a position from which the radiation detector head views a subject disposed on the subject support pallet at least partially through the high aspect ratio beveled edge.

The drawings are provided only for purpose of illustrating the preferred embodiments, and are not to be construed as limiting the invention.

FIG. 1 diagrammatically shows a gamma camera and an associated patient pallet.

FIGS. 2 and 3 diagrammatically show perspective and end views, respectively, of a rigid thin sheet component of the patient pallet of FIG. 1.

FIG. 4 diagrammatically shows an end view of a high aspect ratio bevel or chamfer of the rigid thin sheet component of the patient pallet of FIG. 1 with certain dimensions labeled.

FIGS. 5 and 6 diagrammatically show perspective and end views, respectively, of the patient pallet of FIG. 1.

FIG. 7 diagrammatically shows an end view of a high aspect ratio bevel or chamfer region of the patient pallet of FIG. 1.

Figure 1:
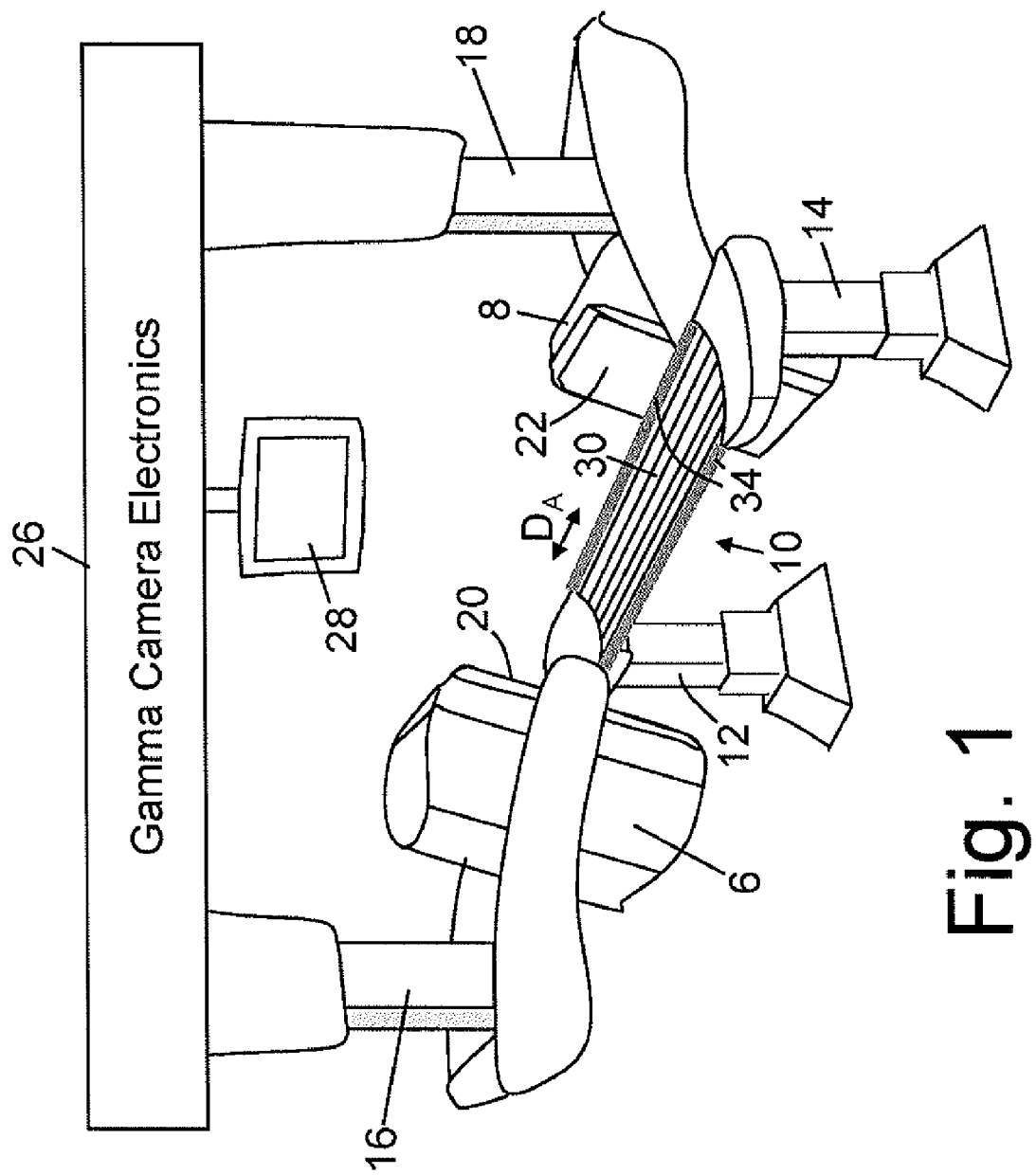
Figure 2:
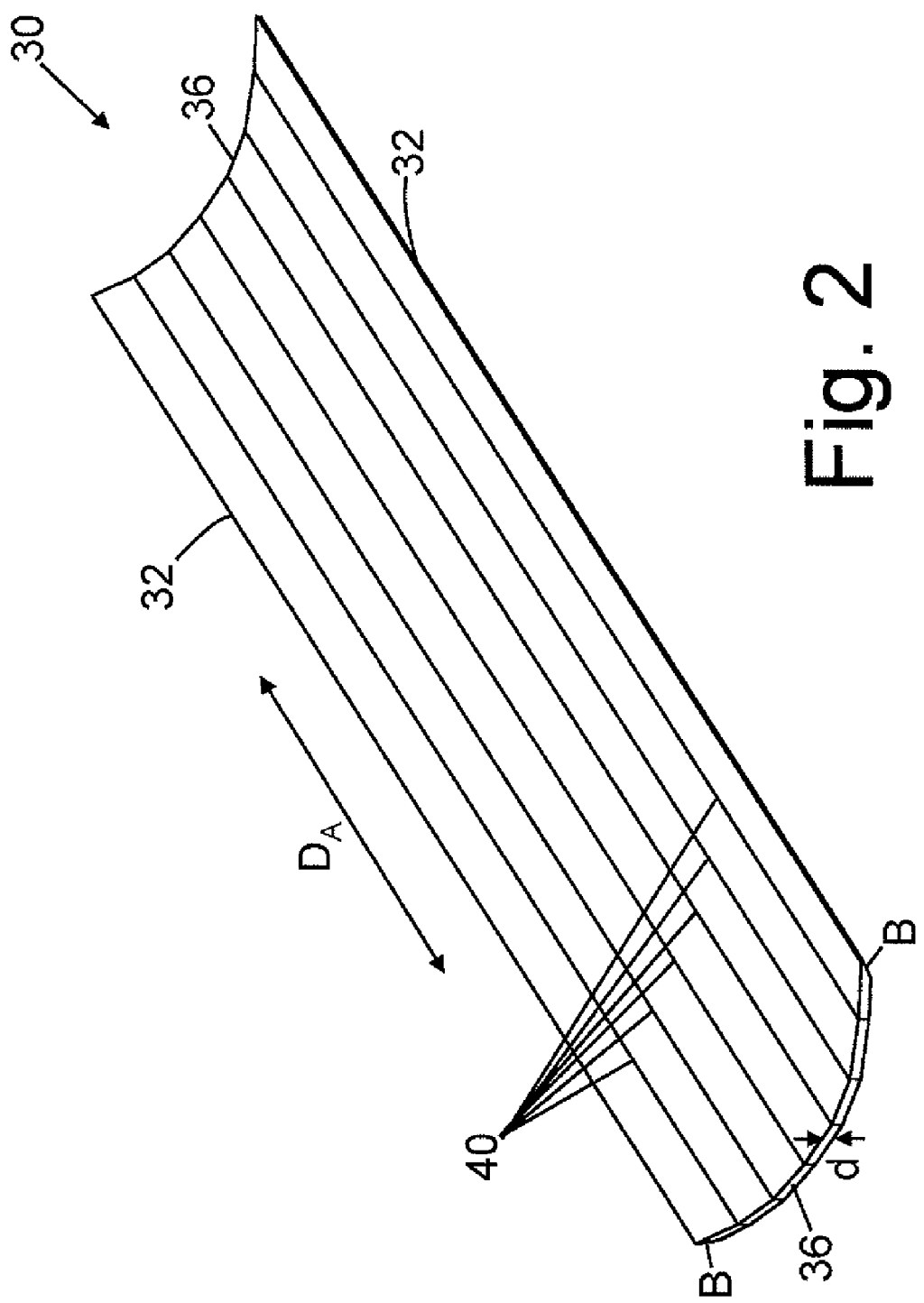
Figure 5:
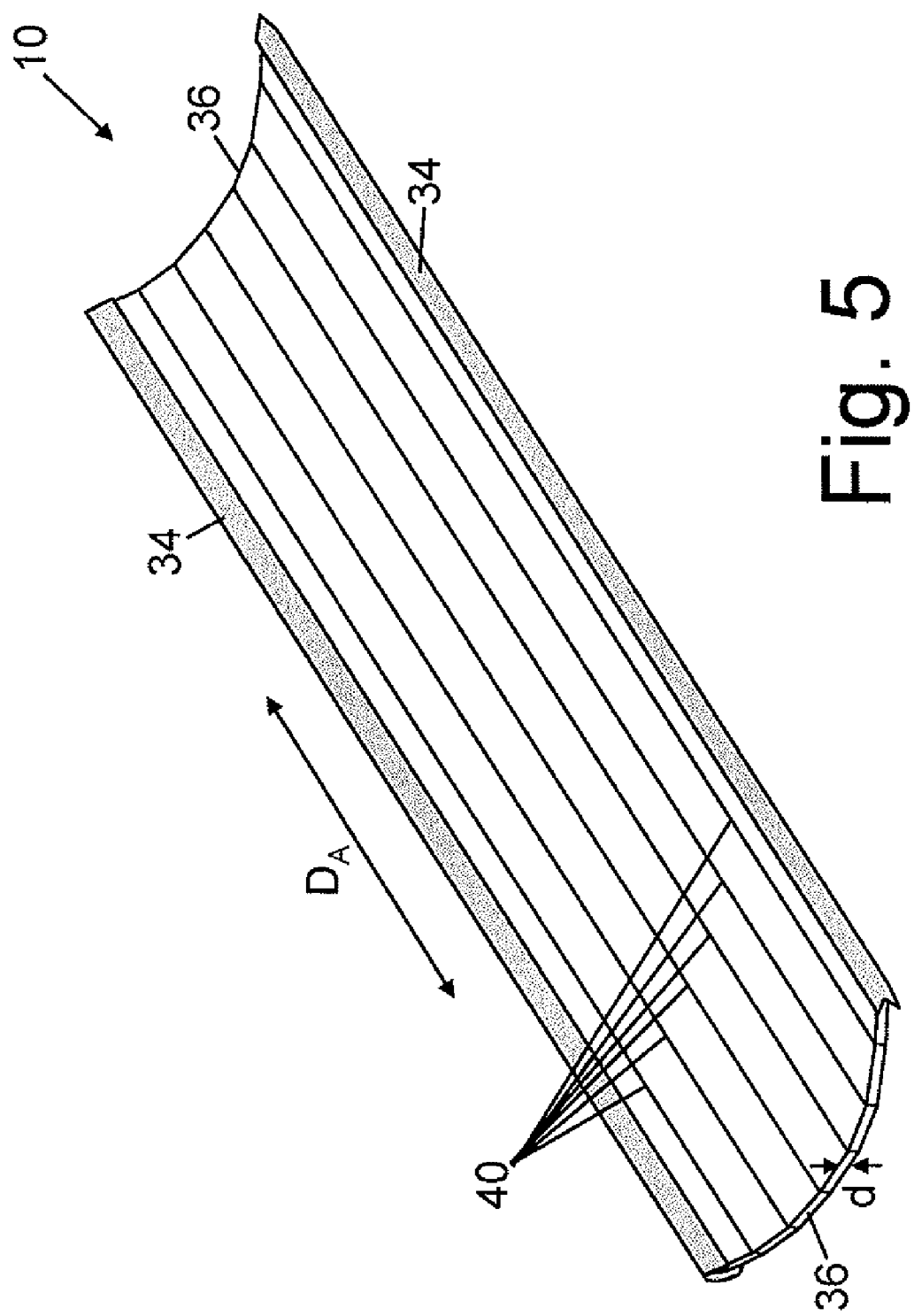

With reference to FIG. 1, a gamma camera includes one or more radiation detector heads 6, 8 configured to be locatable at a range of angles around a subject support pallet 10. While two radiation detector heads 6, 8 are shown in FIG. 1, the number of radiation detector heads can be as few as one radiation detector head, or as many as three, four, five, six, or more radiation detector heads. A pallet support including two pallet support pillars 12, 14 are configured to support the subject support pallet 10 generally horizontally in an elevated position respective to a floor. The two illustrative radiation detector heads 6, 8 are configured to be locatable at a range of angles around the subject support pallet 10 by the use of respective robotic arms 16, 18, which enable the radiation detector heads 6, 8 to be moved, tilted, rotated, canted, or otherwise manipulated to arrange radiation-sensitive faces 20, 22 of the respective radiation detector heads 6, 8 to view a subject disposed on the subject support pallet 10. The robotic arms 16, 18 also enable movement of the radiation-sensitive faces 20, 22 toward or away from the subject disposed on the subject support pallet 10, and still further enable movement of the radiation detector heads 6, 8 in an axial direction $D_A$ along the axial length of the subject support pallet 10, or at least along some portion of the axial length of the subject support pallet 10.

The radiation detector heads 6, 8 are shown in FIG. 1 in a suitable position for acquiring a planar scan by moving the radiation detector heads 6, 8 axially along the axial direction $D_A$ while the radiation detector heads 6, 8 acquire imaging data. In a single photon emission computed tomography (SPECT) imaging modality, the radiation detector heads 6, 8 are moved at least partway around the subject disposed on the subject support pallet 10. Other imaging modalities are also contemplated. Instead of the illustrated arrangement in which the robotic arms 16, 18 are mounted on a ceiling track (not shown), the robotic arms can instead be mounted to a vertical circular gantry or other structure, or can be mounted to or in an annular rotatable gantry, or so forth.

The robotic arms 16, 18 are operated by gamma camera electronics 26 (diagrammatically indicated in FIG. 1) to move one or both radiation detector heads 6, 8 (or more, if more than two radiation detector heads are provided) along a path or trajectory of an imaging data acquisition scan. Imaging data are acquired using the radiation detector heads 6, 8 during the scan. In continuous imaging modes, such data are acquired simultaneously with movement of the radiation detector heads 6, 8. In a step-and-shoot mode, the radiation detector heads 6, 8 are paused at successive stationary positions along the path or trajectory, and imaging data are acquired while the radiation detector heads 6, 8 are at these stationary positions. The imaging data are typically in the form of projection data. The radiation-sensitive faces 20, 22 have pinhole collimators, honeycomb collimators, or other radiation-collimating elements or structures that define a linear or small-angle conical field-of-view for each radiation detection element or area of the radiation-sensitive faces 20, 22. Accordingly, when a radiation detection element detects a radiation event, it is known that the sourcing radioactive decay event is located somewhere along the linear or small-angle field-of-view—thus, the radiation detection defines a "projection" datum.

For either continuous or step-and-shoot acquisition, the imaging data are acquired and stored using gamma camera electronics 26 as an accumulated projection data set. If SPECT imaging data are acquired, then the gamma camera electronics 26 typically applies a filtered backprojection, iterative backprojection, or other suitable image reconstruction algorithm to generate a reconstructed image. For planar imaging, the projection data set suitably defines an image without reconstruction processing, although post-processing is optionally performed to filter or remove noise, rescale intensities, smooth or knit together adjacent fields-of-view to form a composite image, or so forth. The resulting SPECT or planar images are suitably displayed on a monitor 28, printed, transmitted to a physician or other interpretive medical specialist via a hospital network or the Internet, enhanced or manipulated by selected digital image processing, or otherwise processed or used.

During some types of planar or SPECT imaging, one or more radiation detector heads may be positioned underneath or at an oblique angle below the subject, such that the radiation detector head views the subject through the subject support pallet 10. For example, in the configuration of FIG. 1 the radiation detector head 8 is arranged at an oblique angle below the subject such that the radiation detector head 8 views the subject at least partially through the subject support pallet 10. Accordingly, the subject support pallet 10 should be substantially transparent to the gamma rays seen by the radiation detector heads 6, 8. Additionally, to optimize resolution and enhance signal strength the radiation detector head arranged underneath or at an oblique angle below the subject should be as close to the subject as feasible. These considerations motivate toward making the subject support pallet 10 thin.

With continuing reference to FIG. 1 and with further reference to FIGS. 2-7, the subject support pallet 10 includes a rigid thin sheet 30 having strength-enhancing curvature transverse to the axial direction $D_A$ and a thickness d that is preferably less than six millimeters, and is more preferably less than or about four millimeters. An edge 32 of the rigid thin sheet 30 is a chamfered or beveled edge 32 that has a high aspect ratio chamfer or bevel B to reduce or blur edge artifacts in the acquired image or images. Because of the thinness of the rigid thin sheet 30 and the high aspect ratio bevel B, the edge 32 is a sharp edge that could cut or otherwise injure the subject or medical personnel. Optionally, a protective covering 34 is disposed over the beveled edge 32 to reduce a likelihood of injurious contact with the high aspect ratio beveled edge 32. The illustrated rigid thin sheet 30 has beveled edges on both sides running parallel with the axial direction $D_A$; however, it is contemplated to have only one of the two edges beveled. In the illustrated embodiment, axial end edges 36 are not beveled; however, if imaging that views through one or both axial ends 36 is contemplated, then one or both axial ends 36 is optionally also beveled with a bevel comparable with the bevel B.

The term "rigid" as used herein with respect to the rigid thin sheet 30 is intended to encompass any sheet having sufficient rigidity to support a human subject with the rigid thin sheet 30 supported in a manner suitable for nuclear imaging using the gamma camera of FIG. 1 or another suitable imaging system. It is contemplated that the rigid thin sheet 30 may exhibit some flexing or bending responsive to the weight of a supported human subject, for example if the rigid thin sheet 30 supports a human subject in a cantilevered arrangement. It is contemplated that the rigid thin sheet 30 may exhibit some bowing in the middle, for example if the rigid thin sheet supports a human subject with the rigid thin sheet secured at both ends. In some embodiments, the rigid thin sheet 30 is an aluminum sheet (where, as used herein, "aluminum" is intended to encompass aluminum alloys). In some embodiments, the rigid thin sheet 30 is a carbon fiber sheet. Other relatively rigid materials made up of atoms having relatively low atomic weight (and hence typically exhibiting relatively low gamma radiation absorption) are also contemplated.

The illustrated rigid thin sheet 30 has a uniform thickness except where the bevel B thins the sheet. A rigid thin sheet of varying thickness is also contemplated. For example, the rigid thin sheet may be thicker at the edges than near the center, such that the thin central region facilitates close imaging of the spine. For a rigid thin sheet of non-uniform thickness, the sheet thickness dimension d denotes the thickness of the sheet near the beveled edge but outside of the bevel region.

The strength-enhancing curvature transverse to the axial direction $D_A$ can be formed as a continuous curvature (not shown) using a suitable sheet metal shaping apparatus. In the illustrated embodiment, the strength-enhancing curvature transverse to the axial direction $D_A$ is formed as a plurality of parallel small-angle bends 40 oriented parallel with the axial direction $D_A$. The small-angle bends 40 are readily formed into a planar aluminum sheet using a sheet metal brake, for example.

The bevel B of the beveled edge 32 is configured to reduce or blur edge artifacts in the acquired image or images. The bevel typically has an aspect ratio x:y of about 2:1 or higher, and more preferably about 3:1 or higher, where "x" is a first dimension of the bevel along the sheet transverse to the edge and "y" is a second dimension of the bevel transverse to the sheet. In some embodiments, the dimension "x" is at least about 10 millimeters, and more preferably at least about 20 millimeters. Relating the bevel dimension "x" to the image resolution, the bevel dimension "x" should be at least about ten times larger than a pixel or voxel resolution of the gamma camera to facilitate reduction or blurring of edge artifacts, and is more preferably at least about twenty times larger than the pixel or voxel resolution of the gamma camera. By having the dimension "x" of these dimensions, it is assured that the transition from the region where gamma rays pass through the rigid thin sheet 30 to the region where gamma rays do not pass through the rigid thin sheet 30 is spread out over several pixels or voxels, such as about 10-20 pixels or voxels.

The thickness d of rigid thin sheet 30 is preferably less than six millimeters, and more preferably less than or about four millimeters. This imposes an upper limit on the dimension "y" of the bevel aspect ratio x:y. In FIG. 4, the dimension "y" of the bevel B together with a remaining original edge portion "$y_e$" of the original edge equals the thickness d of the rigid thin sheet. The remaining original edge portion "$y_e$" is small. In general, $y_e < y$, and more preferably $y_e \ll y$. The bevel height "y" is preferably at least about four-fifths of the sheet thickness d, and is more preferably at least about nine-tenths of the sheet thickness d. In some embodiments it is contemplated for the bevel height "y" to equal the sheet thickness d, such that the dimension "$y_e$" to be zero, that is, for the bevel to entirely consume the original edge of the rigid thin sheet. In view of the upper limit imposed by the sheet thickness d on the dimension "y", to obtain the desired large dimension "x" the bevel aspect ratio is preferably about 2:1 or higher, or more preferably about 3:1 or higher. The illustrated high aspect ratio bevel B is a planar bevel, which is readily formed and provides a uniform thickness reduction gradient along the dimension "x" to facilitate reduction or blurring of the image edge artifact. However, otherwise-shaped bevels such as quadratic or hyperbolic bevels are also contemplated.

The illustrated rigid thin sheet 30 has a generally concave top-side surface and a generally convex bottom-side surface due to the strength-enhancing curvature of the rigid thin sheet 30. (The general concavity and general convexity are in the direction transverse to the axial direction $D_A$ since the strength-enhancing curvature is in the direction transverse to the axial direction $D_A$. The illustrated rigid thin sheet 30 has no curvature along the axial direction $D_A$, and hence is generally straight along the axial direction $D_A$.) In the illustrated embodiment, the high aspect ratio bevel B is disposed on the bottom-side surface of the pallet. This advantageously provides maximum top-side surface area, and also is believed to provide relatively better reduction or blurring in the image edge artifact as compared with a bevel disposed partially or wholly on the top-side. However, disposing some or all of the bevel on the top-side surface is also contemplated.

The protective covering 34 is optionally disposed over the beveled edge 32 to reduce a likelihood of injurious contact with the high aspect ratio beveled edge 32. The protective covering 34 is substantially transparent to gamma radiation, and in some embodiments has a generally rounded surface to enhance its protective nature. In some embodiments, the protective covering 34 is made of a plastic material. In some embodiments, the protective covering 34 is made of a polyethylene material. In some embodiments, the protective covering 34 is made of an ultra-high molecular weight (UHMW) polymeric material. In some embodiments, the protective covering 34 is a linear bar cap that is fitted over the beveled edge 32. Optionally, an adhesive is used to retain the bar cap on the beveled edge 32. Alternatively, a frictional fit is relied upon. In other embodiments, the protective covering 34 is formed by potting, molding, or so forth. In another approach, the entire pallet could be covered with a polymer sealant or coating, preferably thicker at the beveled edge.

Figure 9:
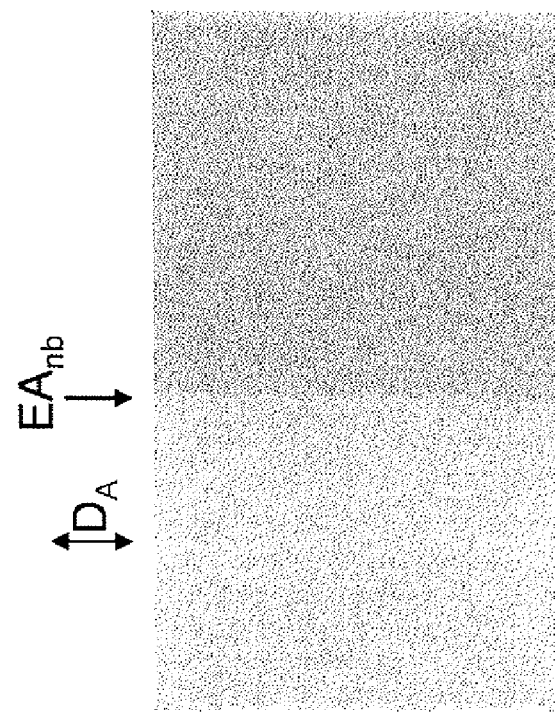
FIG. 9 shows a flood field image acquired using a gamma camera with the radiation detector head looking partially through a edge region of a patient pallet that has no high aspect ratio bevel or chamfer.
Figure 8:
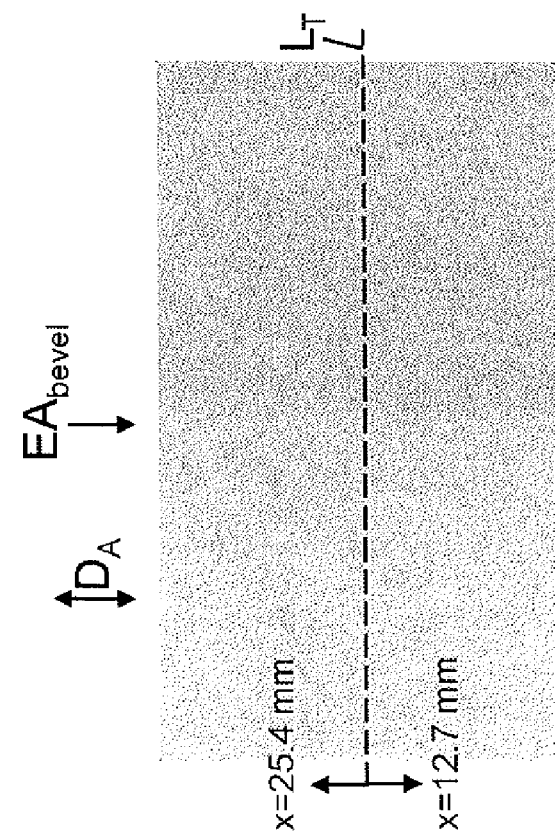
FIG. 8 shows a flood field image acquired using a gamma camera with the radiation detector head looking partially through a high aspect ratio bevel or chamfer region of a patient pallet. In the demonstrative pallet imaged in FIG. 8, the upper portion and lower portion have different chamfer aspect ratios.

With reference to FIGS. 8 and 9, the image edge artifact reduction or blurring is illustrated. FIGS. 8 and 9 each show a planar image taken through the edge of a pallet having thickness of about 3.3 millimeters, with the radiation detector head oriented at an oblique angle of about 45° below the plane of the pallet. The axial direction $D_A$ is vertical in both FIGS. 8 and 9, and the axial extent of the images is approximately 40 centimeters. The image of FIG. 9 shows an edge artifact $EA_{nb}$ corresponding to an axial edge of a conventional aluminum pallet that does not include a bevel. That is, the edge that formed the edge artifact $EA_{nb}$ was not beveled. As seen in FIG. 9, the edge artifact $EA_{nb}$ is an abrupt intensity discontinuity, reflecting the abrupt change in gamma ray absorption at the abrupt unbeveled edge of the conventional pallet.

By contrast, the image of FIG. 9 shows an edge artifact $EA_{bevel}$ corresponding to a beveled axial pallet edge. For illustrative purposes, the axial edge of the pallet imaged in FIG. 8 had a step change in the bevel aspect ratio x:y at about the location of the dashed horizontal transition line $L_T$ superimposed on FIG. 8. Above the transition line $L_T$ the bevel had an aspect ratio x:y of about 8:1, corresponding to the dimension "x" being about 25.4 millimeters. Below the transition line $L_T$ the bevel had an aspect ratio of about 4:1, corresponding to the dimension "x" being about 12.7 millimeters. As seen in FIG. 8, the edge artifact $EA_{bevel}$ is a less abrupt intensity discontinuity, that is, more blurred, compared with the edge artifact $EA_{nb}$ of FIG. 9, reflecting the more gradual change in gamma ray absorption across the beveled edge. Moreover, it is noted that blurring of the edge artifact $EA_{bevel}$ is about the same for the 8:1 bevel as compared with the lower aspect ratio 4:1 bevel. The imaging used in FIGS. 8 and 9 had a resolution of about 2 millimeters; accordingly, the dimension "x" was several times larger than the resolution even for the relatively lower aspect ratio 4:1 bevel.

In the illustrated embodiment the entire edge 32 is beveled with the bevel B. This is generally advantageous. However, some diagnosticians may prefer to have an unblurred artifact similar to the artifact $EA_{nb}$ rather than a blurred artifact similar to the edge artifact $EA_{bevel}$. Such diagnosticians may, for example, prefer to know precisely where the edge artifact is, rather than having a blurred edge artifact whose precise location is not readily determined. Still further, some diagnosticians may want to be able to compare a region in which the edge artifact is blurred with another nearby region in which the edge artifact is unblurred. To achieve these possibilities, it is contemplated for the bevel B to be present along only a portion of the edge 32. For example, the bevel B can be included intermittently, with for example an axial length of ten centimeters beveled, followed by an axial length of ten centimeters unbeveled, and so forth. It is further contemplated for the amount of beveling to be varied along the edge 32.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A pallet for use in conjunction with a gamma camera with a finest resolution $R_F$, the pallet comprising:
   a rigid sheet with a bevel defined along at least a portion of a longitudinal edge of the rigid sheet, the bevel having a length transverse to the longitudinal edge which is at least about ten times larger than the finest resolution $R_F$ of the gamma camera.
   wherein the bevel has an aspect ratio x:y of at least 3:1 where "x" is the length of the bevel and "y" is less than the thickness of the rigid sheet adjacent the bevel.

2. The pallet as set forth in claim 1, wherein the rigid sheet includes a strength-enhancing curvature transverse to an axial direction.

3. The pallet as set forth in claim 1, wherein the bevel tapers toward the longitudinal edge such that a thickness at the edge is zero or a small fraction of a thickness of the rigid sheet adjacent the bevel.

4. A pallet for use in conjunction with a gamma camera, the pallet comprising:
   a rigid sheet having a thickness of less than six millimeters and a strength-enhancing curvature transverse to an axial direction, at least a portion of an edge of the rigid sheet having a bevel with a length "x" along the sheet of at least about ten millimeters and a height "y" of at least about four-fifths of the sheet thickness;
   wherein the bevel has an aspect ratio x:y of at least 3:1.

5. The pallet as set forth in claim 4, further including:
   a protective covering disposed over the beveled edge.

6. The pallet as set forth in claim 4, wherein the bevel has a height equal to the sheet thickness such that there is no remaining original edge portion.

7. The pallet as set forth in claim 4, wherein the bevel has a length along the sheet transverse to the edge of at least about twenty millimeters.

8. The pallet as set forth in claim 4, wherein the bevel has a length along the sheet that is at least about ten times larger than a pixel or voxel resolution of the gamma camera.

9. The pallet as set forth in claim 4, wherein the bevel has a length along the sheet transverse to the edge that is at least about twenty times larger than a pixel or voxel resolution of the gamma camera.

10. The pallet as set forth in claim 4, wherein the bevel is a planar bevel.

11. The pallet as set forth in claim 5, wherein the rigid sheet has a generally concave top-side surface and a generally convex bottom-side surface due to the strength-enhancing curvature of the rigid sheet, and the bevel is disposed on the bottom-side surface of the pallet.

12. The pallet as set forth in claim 4, wherein the strength-enhancing curvature transverse to the axial direction is selected from a group consisting of (i) a continuous curvature transverse to the axial direction, and (ii) a plurality of parallel small-angle bends in the rigid sheet oriented parallel with the axial direction.

13. A pallet for use in conjunction with a gamma camera, the pallet comprising:
   a rigid sheet having a thickness of less than six millimeters and a strength-enhancing curvature transverse to an axial direction, at least a portion of an edge of the rigid sheet having a bevel with a length along the sheet of at least about ten millimeters and a height of at least about four-fifths of the sheet thickness; and
   a protective covering disposed over the beveled edge;
   wherein the rigid sheet is an aluminum or carbon fiber sheet and the protective covering comprises a plastic material.

14. The pallet as set forth in claim 13, wherein the bevel has a height equal to the sheet thickness such that there is no remaining original edge portion.

15. The pallet as set forth in claim 13, wherein the bevel has a length along the sheet transverse to the edge of at least about twenty millimeters.

16. The pallet as set forth in claim 13, wherein the rigid sheet has a generally concave top-side surface and a generally convex bottom-side surface due to the strength-enhancing curvature of the rigid sheet, and the bevel is disposed on the bottom-side surface of the pallet.

17. An imaging system comprising:
   a pallet as set forth in claim 4; and
   at least one radiation detector head arranged to view the pallet.

18. An imaging system comprising:
   a subject support pallet including a rigid sheet having strength-enhancing curvature transverse to an axial direction, an edge of the rigid sheet having a bevel with an aspect ratio x:y where dimension "x" is along the rigid sheet and is at least ten millimeters and "y" is transverse to the sheet and is at least about four-fifths of a thickness of the rigid sheet;
   a pallet support configured to support the subject support pallet generally horizontally in an elevated position respective to a floor; and
   at least one radiation detector head selectively locatable at a position from which the radiation detector head views a subject disposed on the subject support pallet at least partially through the high aspect ratio beveled edge.

19. The imaging system as set forth in claim 18, wherein the pallet support is selected from a group consisting of: (i) a double-ended support configured to support the subject support pallet at two locations spaced apart along the axial direction, and (ii) a cantilever support configured to support the subject support pallet at one axial end in a cantilevered arrangement.

20. The imaging system as set forth in claim 18, wherein the bevel aspect ratio x:y is at least about 3:1.

21. The imaging system as set forth in claim 18, wherein the thickness of the rigid sheet is less than six millimeters.

22. The imaging system as set forth in claim 18, wherein the subject support pallet further comprises:
   a protective covering disposed over the beveled edge to reduce a likelihood of injurious contact with the beveled edge.

23. An imaging system comprising:
   a pallet as set forth in claim 13; and
   at least one radiation detector head arranged to view the pallet.

* * * * *